US00PP18698P3

(12) United States Plant Patent
Bessho

(10) Patent No.: US PP18,698 P3
(45) Date of Patent: Apr. 1, 2008

(54) ***PETUNIA* PLANT NAMED 'KAKEGAWA S84'**

(50) Latin Name: *Petunia hybrida*
Varietal Denomination: Kakegawa S84

(75) Inventor: Masao Bessho, Marslev (DK)

(73) Assignee: Sakata Seed Corporation, Yokohama (JP)

( * ) Notice: Subject to any disclaimer, the term of this patent is extended or adjusted under 35 U.S.C. 154(b) by 89 days.

(21) Appl. No.: 11/352,964

(22) Filed: Feb. 13, 2006

(65) Prior Publication Data

US 2007/0192920 P1 Aug. 16, 2007

(51) Int. Cl.
*A01H 5/00* (2006.01)

(52) U.S. Cl. ..... Plt./356

(58) Field of Classification Search ..... Plt./263, Plt./356

See application file for complete search history.

*Primary Examiner*—Howard J. Locker
(74) *Attorney, Agent, or Firm*—Jondle & Associates, P.C.

(57) ABSTRACT

A *petunia* cultivar particularly distinguished by pink flowers with a red inner corolla throat and a mounding growth habit is disclosed.

1 Drawing Sheet

Genus and species: *Petunia hybrida.*
Variety denomination: 'Kakegawa S84'.

BACKGROUND OF THE NEW PLANT

The present invention comprises a new and distinct cultivar of *petunia,* botanically known as *Petunia hybrida,* and hereinafter referred to by the cultivar name 'Kakegawa S84'. 'Kakegawa S84' originated from a whole plant off-type of 'SAIPET93', an unpatented proprietary *petunia* plant in Salinas, Calif. in 2003. 'SAIPET93' originated from a hybridization between '001-93', a proprietary *petunia* plant with medium flower size and pink flower color, and '002-93', a proprietary *petunia* plant with magenta flowers and a creeping growth habit.

$F_1$ and $F_2$ generations resulting from the hybridization were grown. Segregation in the $F_2$ generation resulted in plants that had either pink or magenta flower color, medium or small flower size, and either a creeping, mounding, or cascading growth habit. An F3 generation was produced. From the F3 generation, plants were selected that exhibited a pink flower color and creeping growth habit. The selections were then subjected to several rounds of sexual propagation for the purpose of fixing the desirable traits through successive generations of sexual reproduction. The F10 generation resulted in a sexually reproduced *petunia* with pink flower color and a creeping growth habit named '004-93'.

A second hybridization was performed using '004-93' as the male parent and another proprietary *petunia* plant with a medium flower size and a light pink flower color named '003-93' as the female parent. The resulting $F_1$ hybrid had a medium flower size and a light pink flower color. The hybrid was named 'SAIPET93'.

In 2003, a sport of 'SAIPET93' was noticed in Salinas, Calif. The sport had a pink with red inner corolla throat and tube. The sport was maintained by way of shoot-tip cuttings in Salinas, Calif. and was observed to have its distinct characteristics remain stable through successive generations of asexual reproduction. The sport was then named 'Kakegawa S84'. 'Kakegawa S84' has been found to retain its distinctive characteristics after three years and five cycles of vegetative propagation.

Plant Breeder's Rights for this cultivar were applied for in Canada on Apr. 19, 2005.

DESCRIPTION OF PHOTOGRAPHS

This new *petunia* plant is illustrated by the accompanying photographs which show blooms and foliage of the plant in full color, the colors shown being as true as can be reasonably obtained by conventional photographic procedures.

DESCRIPTION OF THE NEW CULTIVAR

Figure 1:
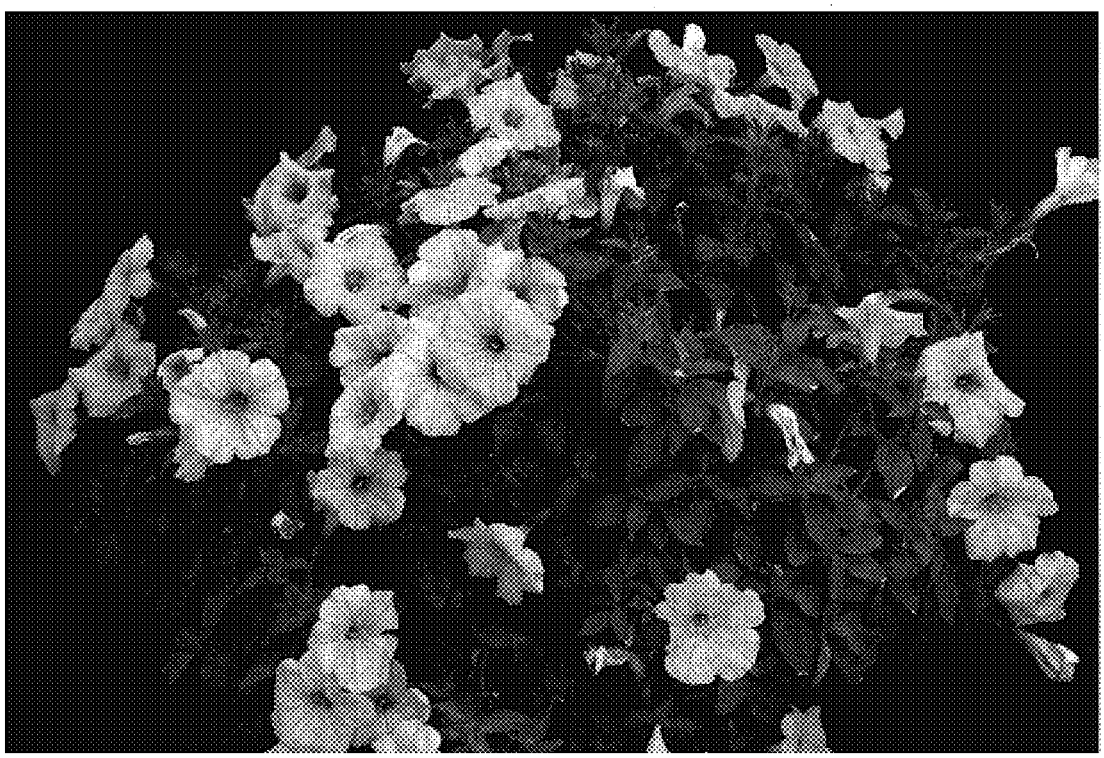
FIG. 1 shows the overall plant habit, including blooms, buds and foliage.
Figure 2:
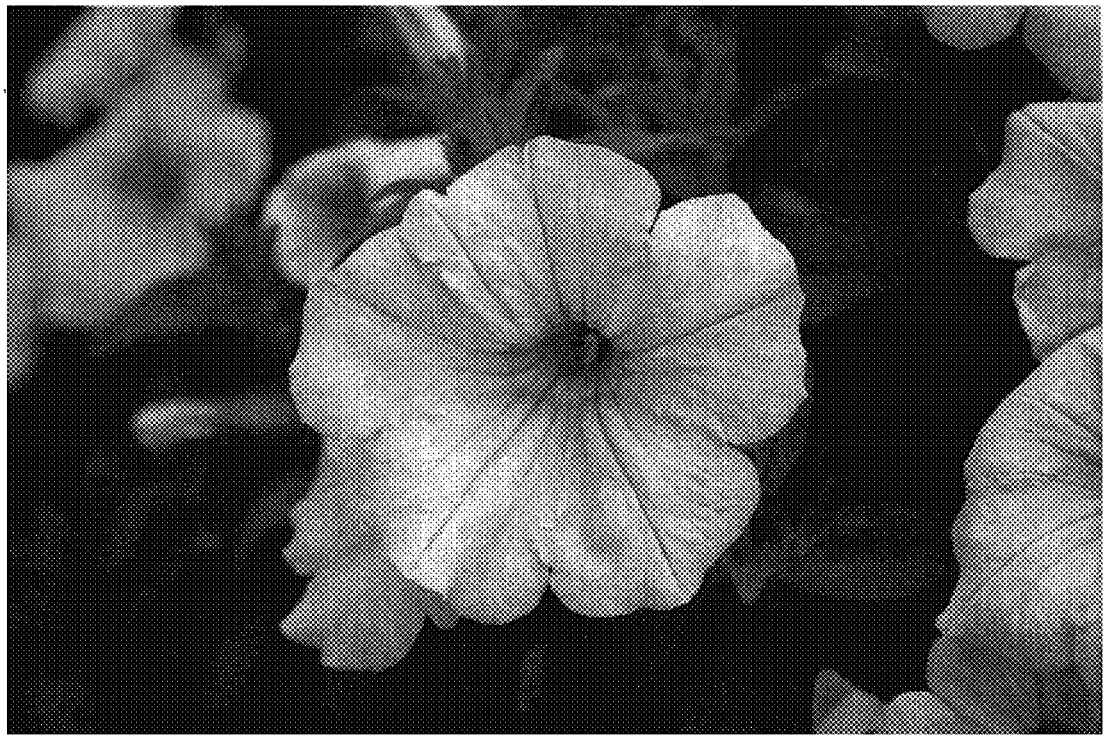
FIG. 2 shows the mature flower.

The following detailed descriptions set forth the distinctive characteristics of 'Kakegawa S84'. The data which defines these characteristics were collected from asexual reproductions carried out in Salinas, Calif. Data was collected on plants in 6 inch pots four months after rooted cuttings were transplanted. Plants were pinched once during growth. Color references are primarily to the RHS Colour Chart of The Royal Horticultural Society of London (RHS) ($4^{th}$ ed). Anatomic labels are from The Cambridge Illustrated Glossary of Botanical Terms, by M. Hickey and C. King, Cambridge University Press.

DETAILED BOTANICAL DESCRIPTION

Classification:
*Family.*—Solanaceae.
*Botanical.—Petunia hybrida.*
*Common name.—Petunia.*

Parentage: Whole plant off-type of 'SAIPET93'.

Growth: The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 second every 30 minutes until sufficient roots were formed. Plants were propagated from vegetative cuttings, and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigations. Pots were top-dressed with a dry, slow release fertilizer containing 20% nitrogen, 10% phosphorus and 18% potassium. The typical average air temperature was 24° C.

Plant description:

*Life cycle.*—Annual/tender perennial in warm climates.
*Habit.*—Semi-decumbent (mounding): freely branching.
*Height.*—34.0 cm.
*Spread.*—61.0 cm.
*Time to produce a rooted cutting.*—About 4 weeks.
*Time to produce a finished flowering plant.*—6–8 weeks.
*Flowering requirements.*—Will flower as long as the temperature is above 13° C. and there is greater than 12 hours of daylight.

Branches:

*Number of branches.*—About 12 basal branches; many secondary branches.
*Length of branches.*—25.0 cm to 30.0 cm.
*Diameter of branches.*—0.2 cm to 0.3 cm.

Stems:

*Description.*—Pliable; circular cross-section.
*Color.*—RHS 144B (yellow-green).
*Diameter.*—0.6 cm.
*Stem length.*—1.0 cm from soil line to first node.
*Internode length.*—0.6 cm at the bottom of the plant and 2.1 cm at the top of the plant.
*Anthocyanin.*—Absent.
*Texture.*—Heavily pubescent.
*Pubescence color.*—RHS N155A (white).

Leaves:

*Arrangement.*—Alternate.
*Attachment.*—Petiolate.
*Apex.*—Acute.
*Base.*—Attenuate.
*Color.*—Upper surface: RHS 146B (yellow-Green). Lower surface: RHS 143A (green).
*Margin.*—Entire.
*Size.*—Length: 2.5 cm to 3.0 cm. Width: 1.4 cm to 1.5 cm.
*Shape.*—Elliptical.
*Texture.*—Dull, heavily pubescent.
*Surface pubescence color.*—RHS N155A (white).
*Variegation.*—Absent.
*Venation.*—Type: Pinnate. Color: Upper surface: RHS 145B (yellow-green). Lower surface: RHS 145B (yellow-green).
*Fragrance.*—Weak.
*Petiole.*—Length: 0.5 cm. Diameter: 0.2 cm. Color: RHS 145B (yellow-green).

Flower buds:

*Color.*—RHS 151C (yellow-green).
*Shape.*—Cylindrical.
*Surface.*—Dull; pubescent.
*Length.*—1.5 cm.
*Diameter.*—0.4 cm.

Flowers:

*Type.*—Flowers continuously; self-cleaning.
*Lastingness of individual bloom.*—5 days.
*Inflorescence type.*—Single flower.
*Fragrance.*—Absent.
*Flower number (per node).*—One.
*Peduncle.*—Color: RHS 144B (yellow-green). Length: 1.5 cm to 3.0 cm. Diameter: 0.45 cm to 0.50 cm.

Calyx (sepals):

*Form.*—5, free.
*Attachment.*—Decurrent.
*Length.*—1.5 cm to 2.0 cm.
*Width.*—0.2 cm.
*Apex.*—Acute.
*Base.*—Cuneate.
*Margin.*—Entire.
*Sepal color.*—Upper surface: Closest to RHS 139B (green). Lower surface: RHS 144B (yellow-green).

Corolla:

*Shape.*—Funnel-shaped with five fused petals.
*Diameter.*—4.4 cm to 6.0 cm.
*Depth.*—3.9 cm to 4.5 cm.
*Tube diameter.*—0.7 cm to 0.9 cm.
*Tube length.*—1.8 cm to 2.3 cm.

Petals:

*Shape.*—Obcordate.
*Size.*—Length: 2.5 cm to 2.6 cm. Width: 2.0 cm to 3.0 cm.
*Apex.*—Acuminate.
*Margin.*—Entire.
*Color of lobes.*—Upper surface: RHS 73B (red-purple). Lower surface: RHS N155A (white).
*Color of tube.*—Inner surface: RHS N155A (white). Outer surface: RHS N155A (white) with RHS N144A (yellow-green) veins. Throat: RHS N74B (red-purple).
*Petal texture.*—Glabrous.

Reproductive organs:

*Stamens.*—Quantity: 5. Form: Arranged adjacent to the pistil. Filament color: RHS N155A (white). Anther color: RHS 161D (grayed-yellow).
*Pollen.*—Amount: Abundant. Description: Powdery. Color: RHS 161D (grayed-yellow).
*Ovary.*—Superior.
*Pistil number.*—One.
*Style color.*—RHS 143B (green).
*Stigma color.*—RHS 143A (green).
*Seed.*—None observed.

Disease and insect resistance: No particular resistance or susceptibility to diseases or insects noted to date.

COMPARISON WITH KNOWN CULTIVARS

'Kakegawa S84' differs from *petunia* plant '003-93' (unpatented), a female ancestor of 'Kakegawa S84', in that 'Kakegawa S84' has a pink flower with a red corolla throat, while '003-93' has a light pink flower.

'Kakegawa S84' differs from *petunia* plant '004-93' (unpatented), a male ancestor of 'Kakegawa S84', in that 'Kakegawa S84' has a pink flower with a red corolla throat, while '004-93' has a pink flower. Additionally, 'Kakegawa S84' has a mounding growth habit while '004-93' has a creeping growth habit.

'Kakegawa S84' is a new and distinct variety of *petunia* owing to its pink with red inner corolla tube flower color. 'Kakegawa S84' is similar to 'SAIPET93' (unpatented), however there are numerous differences as listed in the table below:

TABLE 1

| Comparison of Characteristics between 'Kakegawa S84' and 'SAIPET93' | | |
|---|---|---|
| Characteristic | 'Kakegawa S84' | 'SAIPET93' |
| Flower color | Pink with red inner corolla throat | Pink |
| Propagation method | Shoot-tip cuttings (asexual) | Seed (sexual) |

I claim:

1. A new and distinct cultivar of *petunia* plant named 'Kakegawa S84' as described and shown herein.

* * * * *